(12) United States Patent
Wang et al.

(10) Patent No.: US 7,761,185 B2
(45) Date of Patent: Jul. 20, 2010

(54) REMOTE PRESENCE DISPLAY THROUGH REMOTELY CONTROLLED ROBOT

(75) Inventors: Yulun Wang, Goleta, CA (US); Charles S. Jordan, Santa Barbara, CA (US); Marco Pinter, Santa Barbara, CA (US); Michael C. Chan, Santa Barbara, CA (US)

(73) Assignee: InTouch Technologies, Inc., Goleta, CA (US)

( * ) Notice: Subject to any disclaimer, the term of this patent is extended or adjusted under 35 U.S.C. 154(b) by 960 days.

(21) Appl. No.: 11/542,912

(22) Filed: Oct. 3, 2006

(65) Prior Publication Data

US 2008/0082211 A1   Apr. 3, 2008

(51) Int. Cl.
G05B 15/00 (2006.01)

(52) U.S. Cl. .................................. 700/259
(58) Field of Classification Search ............. 700/245, 700/248–249, 257, 259; 901/1, 46–47
See application file for complete search history.

(56) References Cited

U.S. PATENT DOCUMENTS

| | | | |
|---|---|---|---|
| 3,821,995 A | 7/1974 | Aghnides | |
| 4,413,693 A | 11/1983 | Derby | |
| 4,471,354 A | 9/1984 | Smith | |
| 4,519,466 A | 5/1985 | Shiraishi | |
| 4,638,445 A | 1/1987 | Mattaboni | |
| 4,733,737 A | 3/1988 | Falamak | |
| 4,875,172 A | 10/1989 | Kanayama | |
| 5,073,749 A | 12/1991 | Kanayama | |
| 5,084,828 A | 1/1992 | Kaufman et al. | |
| 5,186,270 A | 2/1993 | West | |
| 5,305,427 A | 4/1994 | Nagata | |
| 5,341,242 A | 8/1994 | Gilboa et al. | |
| 5,341,854 A | 8/1994 | Zezulka et al. | |
| 5,374,879 A | 12/1994 | Pin et al. | |
| 5,419,008 A | 5/1995 | West | |
| 5,486,853 A | 1/1996 | Baxter et al. | |
| 5,510,832 A | 4/1996 | Garcia | |
| 5,544,649 A | 8/1996 | David et al. | |

(Continued)

FOREIGN PATENT DOCUMENTS

CA    2289697 A1    11/1998

(Continued)

OTHER PUBLICATIONS

Baltus et al., "Towards Personal Service Robots for the Elderly", Computer Science and Robotoics.

(Continued)

*Primary Examiner*—Kim T Nguyen
(74) *Attorney, Agent, or Firm*—Ben J. Yorks; Irell & Manella LLP

(57) ABSTRACT

A robot system that includes a robot and a remote station. The robot and remote station contain monitors, cameras, speakers and microphones that allow for two-way videoconferencing between a physician at the remote station and a patient in the vicinity of the robot. The system also includes a patient monitor that displays patient information such as an x-ray. The patient monitor can be seen by the patient, and by the physician through the robot camera. The system allows for a physician to remotely review the medical information with the patient.

13 Claims, 8 Drawing Sheets

U.S. PATENT DOCUMENTS

| | | |
|---|---|---|
| 5,572,229 A | 11/1996 | Fisher |
| 5,630,566 A | 5/1997 | Case |
| 5,636,218 A | 6/1997 | Ishikawa et al. |
| 5,762,458 A | 6/1998 | Wang et al. |
| 5,786,846 A | 7/1998 | Hiroaki |
| 5,802,494 A | 9/1998 | Kuno |
| 5,838,575 A | 11/1998 | Lion |
| 5,857,534 A | 1/1999 | DeValult et al. |
| 5,917,958 A | 6/1999 | Nunally et al. |
| 5,959,423 A | 9/1999 | Nakanishi et al. |
| 5,966,130 A | 10/1999 | Benman, Jr. |
| 6,006,946 A | 12/1999 | Williams et al. |
| 6,036,812 A | 3/2000 | Williams et al. |
| 6,133,944 A | 10/2000 | Braun et al. |
| 6,135,228 A | 10/2000 | Asada et al. |
| 6,170,929 B1 | 1/2001 | Wilson et al. |
| 6,211,903 B1 | 4/2001 | Bullister |
| 6,219,587 B1 | 4/2001 | Ahlin et al. |
| 6,232,735 B1 | 5/2001 | Baba et al. |
| 6,233,735 B1 | 5/2001 | Ebihara |
| 6,259,806 B1 | 7/2001 | Green |
| 6,292,713 B1 | 9/2001 | Jouppi et al. |
| 6,304,050 B1 | 10/2001 | Skaar et al. |
| 6,346,950 B1 | 2/2002 | Jouppi |
| 6,369,847 B1 | 4/2002 | James et al. |
| 6,430,471 B1 | 8/2002 | Kintou et al. |
| 6,438,457 B1 | 8/2002 | Yokoo et al. |
| 6,463,361 B1 | 10/2002 | Wang et al. |
| 6,474,434 B1 | 11/2002 | Bech |
| 6,491,701 B2 | 12/2002 | Tierney et al. |
| 6,496,099 B2 | 12/2002 | Wang et al. |
| 6,522,906 B1 | 2/2003 | Salisbury et al. |
| 6,532,404 B2 | 3/2003 | Colens |
| 6,535,182 B2 | 3/2003 | Stanton |
| 6,535,793 B2 | 3/2003 | Allard |
| 6,543,899 B2 | 4/2003 | Covannon et al. |
| 6,549,215 B2 | 4/2003 | Jouppi |
| 6,587,750 B2 | 7/2003 | Gerbi et al. |
| 6,594,552 B1 | 7/2003 | Nowlin et al. |
| 6,646,677 B2 | 11/2003 | Noro et al. |
| 6,684,129 B2 | 1/2004 | Salisbury et al. |
| 6,799,065 B1 | 9/2004 | Niemeyer |
| 6,799,088 B2 | 9/2004 | Wang et al. |
| 6,804,656 B1 | 10/2004 | Rosenfeld et al. |
| 6,836,703 B2 | 12/2004 | Wang et al. |
| 6,839,612 B2 | 1/2005 | Sanchez et al. |
| 6,852,107 B2 | 2/2005 | Wang et al. |
| 6,871,117 B2 | 3/2005 | Wang et al. |
| 6,879,879 B2 | 4/2005 | Jouppi et al. |
| 6,892,112 B2 | 5/2005 | Wang et al. |
| 6,925,357 B2 | 8/2005 | Wang et al. |
| 6,995,664 B1 | 2/2006 | Darling |
| 2001/0037163 A1 | 11/2001 | Allard |
| 2001/0054071 A1 | 12/2001 | Loeb |
| 2002/0027597 A1 | 3/2002 | Sachau |
| 2002/0057279 A1 | 5/2002 | Jouppi |
| 2002/0058929 A1 | 5/2002 | Green |
| 2002/0063726 A1 | 5/2002 | Jouppi |
| 2002/0120362 A1 | 8/2002 | Lathan et al. |
| 2002/0130950 A1 | 9/2002 | James et al. |
| 2002/0141595 A1 | 10/2002 | Jouppi |
| 2002/0183894 A1 | 12/2002 | Wang et al. |
| 2003/0048481 A1 | 3/2003 | Kobayashi |
| 2003/0050733 A1 | 3/2003 | Wang et al. |
| 2003/0100892 A1 | 5/2003 | Morley et al. |
| 2003/0114962 A1 | 6/2003 | Niemeyer |
| 2003/0135203 A1 | 7/2003 | Wang et al. |
| 2003/0144649 A1 | 7/2003 | Ghodoussi et al. |
| 2003/0151658 A1 | 8/2003 | Smith |
| 2003/0220541 A1 | 11/2003 | Salisbury et al. |
| 2004/0019406 A1 | 1/2004 | Wang et al. |
| 2004/0117065 A1 | 6/2004 | Wang et al. |
| 2004/0143421 A1 | 7/2004 | Wang et al. |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0174129 A1 | 9/2004 | Wang et al. |
| 2005/0021182 A1 | 1/2005 | Wang et al. |
| 2005/0021183 A1 | 1/2005 | Wang et al. |
| 2005/0021187 A1 | 1/2005 | Wang et al. |
| 2005/0024485 A1 | 2/2005 | Castles et al. |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0052527 A1 | 3/2005 | Remy et al. |
| 2005/0204438 A1* | 9/2005 | Wang et al. .................. 901/1 |
| 2006/0047365 A1 | 3/2006 | Ghodoussi et al. |
| 2006/0064212 A1 | 3/2006 | Thorne |

FOREIGN PATENT DOCUMENTS

| | | |
|---|---|---|
| EP | 0981905 B1 | 1/2002 |
| JP | 07257422 A | 10/1995 |
| JP | 2000-032319 A | 1/2000 |
| JP | 2002-046088 | 2/2002 |
| JP | 2002305743 A | 10/2002 |

OTHER PUBLICATIONS

Bauer, Jeffrey C., "Service Robots in Health Care: The Evolution of Mechanical Solutions to Human Resource Problems", Jun. 2003.

Breslow, Michael J., MD et al., "Effect of a multiple-site intensive care unit telemedicine program on clinical and economic outcome: An alternative paradigm for intensivist staffing", Critical Care Med, Jan. 2004, vol. 32, No. 1, pp. 31-38.

Celi et al., "The eICU: It's not just telemedicine", Critical Care Medicine, vol. 29, No. 8 (Supplement), Aug. 2001.

Cleary et al., "State of the art in surgical robotics: Clinical applications and technology challenges", 2002 Internet, pp. 1-26.

CNN.com/Technology, Paging R.Robot: Machine helps doctors with patients, Sep. 30, 2003, Internet, 1-3.

Davies, "Robotics in Minimally Invasive Surgery", 1995, Internet, pp. 5/1-5/2.

DiGiorgio, James, "Is Your Emergency Department of the 'Leading Edge'?", 2005, Internet, pp. 1-4.

Elhajj et al., "Supermedia in Internet-based telerobotic operations", 2001, Internet, p. 1-14.

Ellison et al., "Telerounding and Patient Satisfaction Following Surgery".

Goldman, Lea, "Machine Dreams", Entrepreneurs, Forbes, May 27, 2002.

Gump, Michael D., "Robot Technology Improves VA Pharmacies", 2001, Internet, pp. 1-3.

Harmo et al., "Moving Eye—Interactive Telepresence Over Internet With a Ball Shaped Mobile Robot", 2000.

Hees, William P., "Communications Design for a Remote Presence Robot", Jan. 14, 2002.

Ishihara, Ken et al., "Intelligent Microrobot DDS (Drug Delivery System) Measured and Controlled by Ultrasonics", 1991, IEEE/RSJ, pp. 1145-1150, vol. 2.

Jouppi, et al., :Mutually-Immersive Audio Telepresence, Audio Engineering Society Convention Paper, presented at 113th Convention Oct. 2002.

Jouppi, Norman P., "First Steps Towards Mutually-Immersive Mobile Telepresence", CSCW '02, Nov. 16-20, 2002, New Orleans LA.

Kanehiro, Fumio et al., Virtual Humanoid Robot Platform to Develop Controllers of Real Humanoid Robots without Porting, 2001,IEEE, pp. 3217-3276.

Kaplan et al., "An Internet Accessible Telepresence".

Kuzuoka et al., "Can the GestureCam Be a Surrogate?"

Lim, Hun-ok et al., Control to Realize Human-like Walking of a Biped Humanoid Robot, IEE 2000, pp. 3271-3276.

Loeb, Gerald, "Virtual Visit: Improving Communication for Those Who Need It Most", 2001.

Mack, "Minimally invasive and robotic surgery", 2001, Internet IEEE, pp. 568-572.

Magne Charge—Smart Power for Electric Vehicles, Internet, Jun. 27, 2002.

Martin, Anya, "Days Ahead", Assisted Living Today, vol. 9, Nov./Dec. 2002, pp. 19-22.

McCardle et al., "The challenge of utilizing new technology in design education", 2000 Internet, pp. 122-127.

Ojha, Anad, "An application of Virtual Reality in Rehabilitation", Jan. 1994, IEEE, pp. 4-6.

Paulos et al., "A World Wide Web Telerobotic Remote Environment Browser", http://vive.cs.berkeley.edu/capek, 1995.

Paulos, Eric John, "Personal Tele-Embodiment", 2001.

Paulos, et al., "Ubiquitous Tele-embodiment: Applications and Implications", International Journal of Human Computer Studies, Jun. 1997, vol. 46, No. 6, pp. 861-877.

Paulos, et al., "Designing Personal Tele-Embodiment", Presented at the IEEE International Conference on Robotics and Animation, Leuven, Belgium, May 20, 1998.

Pin et al., "A New Family of Omnidirectional and Holonomic Wheeled Platforms for Mobile Robots", IEEE, vol. 10, No. 4, Aug. 1994.

Robot Hardware Mobile Robotics Research Group, Edinburgh, "Mobile Robotics Research Group", 2000 Internet, pp. 1-2.

Roland Piquepaille's Technology Trends, "How new technologies are modifying your way of life", 2003, Internet, pp. 1-2.

PYXIS HelpMate®, the Trackless Robotic Courier, Internet, 3 pgs.

"Remote Presence", p. 131-147.

Roy et al., "Towards Personal Service Robots for the Elderly", Internet, Mar. 7, 2002.

Sandt, Frederic et al., "Perceptions for a Transport Robot in Public Environments", 1997, IROS '97.

Stephenson, Gary, "Dr. Robot Tested at Hopkins", 2003, Internet, p. 1.

Stoianovici et al., "Robotic Tools for Minimally Invasive Urologic Surgery", Dec. 2002, Internet, 1-17.

Tendick et al., "Human-Machine Interfaces for Minimally Invasive Surgery", 1997, IEEE, pp. 2771-2776.

Thrun et al, "Probabilistic Algorithms and the Interactive Museum Tour-Guide Robot Minerva", 2000, Internet pp. 1-35.

Tzafestas, et al., "VR-based Teleoperation of a Mobile Robotic Assistant: Progress Report", 2000, Internet, pp. 1-23.

Urquhart, Kim, "InTouch's robotic Companion 'beams up' healthcare experts", Medical Device Daily, vol. 7, No. 39, Feb. 27, 2003, p. 1, 4.

Zipperer, Lorri, "Robotic dispensing system", 1999, Internet, pp. 1-2.

Zorn, Benjamin G., "Ubiquitous Telepresence", http://www.cs.colorado.edu/~zorn/ut/vision/vision.html, Mar. 5, 1996.

* cited by examiner

REMOTE PRESENCE DISPLAY THROUGH REMOTELY CONTROLLED ROBOT

BACKGROUND OF THE INVENTION

1. Field of the Invention

The subject matter disclosed generally relates to a system and method to provide patient consultation by a physician.

2. Background Information

There has been marketed a mobile robot introduced by InTouch-Health, Inc., the assignee of this application, under the trademarks COMPANION, RP-6 and RP-7. The InTouch robot is controlled by a user at a remote station. The remote station may be a personal computer with a joystick that allows the user to remotely control the movement of the robot. Both the robot and remote station have cameras, monitors, speakers and microphones to allow for two-way video/audio communication.

The InTouch robot has been used by physicians to remotely view and communicate with patients in healthcare facilities. The robot monitor displays an image of the doctor to create a tele-presence of the physician. A doctor can move the robot from room to room of the facility to provide consultation and care for the patient. The cameras, monitors, speakers and microphones of the robot and remote station allow the physician to communicate with the patient through speech and visual images.

It is sometimes desirable to review medical information with the patient. For example, it may be desirable to review an x-ray with a patient while providing consultation through the tele-presence robot. The medical information can be provided to the patient by a medical assistant who is present at the remote patient location. This requires that the assistant be present in the room. Alternatively, the robot monitor can display the medical information. Unfortunately, when the information is displayed by the robot monitor the physican's video image is no longer displayed and the robot does not provide a tele-presence of the doctor. It would be desirable to provide a system that allows a mobile robot to project a presence of a physician while reviewing medical information of a patient without requiring a medical assistant.

BRIEF SUMMARY OF THE INVENTION

A robot system that includes a remote station coupled to a mobile robot. The mobile robot has a robot monitor that displays an image captured by a remote station camera. Likewise, the remote station has a monitor that displays an image captured by a robot camera. The system further includes a patient monitor that displays patient information that can be captured by the robot camera.

DETAILED DESCRIPTION

Disclosed is a robot system that includes a robot and a remote station. The robot and remote station contain monitors, cameras, speakers and microphones that allow for two-way videoconferencing between a physician at the remote station and a patient in the vicinity of the robot. The system also includes a patient monitor that displays patient information such as an x-ray. The patient monitor can be seen by the patient, and by the physician through the robot camera. The system allows for a physician to remotely review the medical information with the patient.

Figure 1:
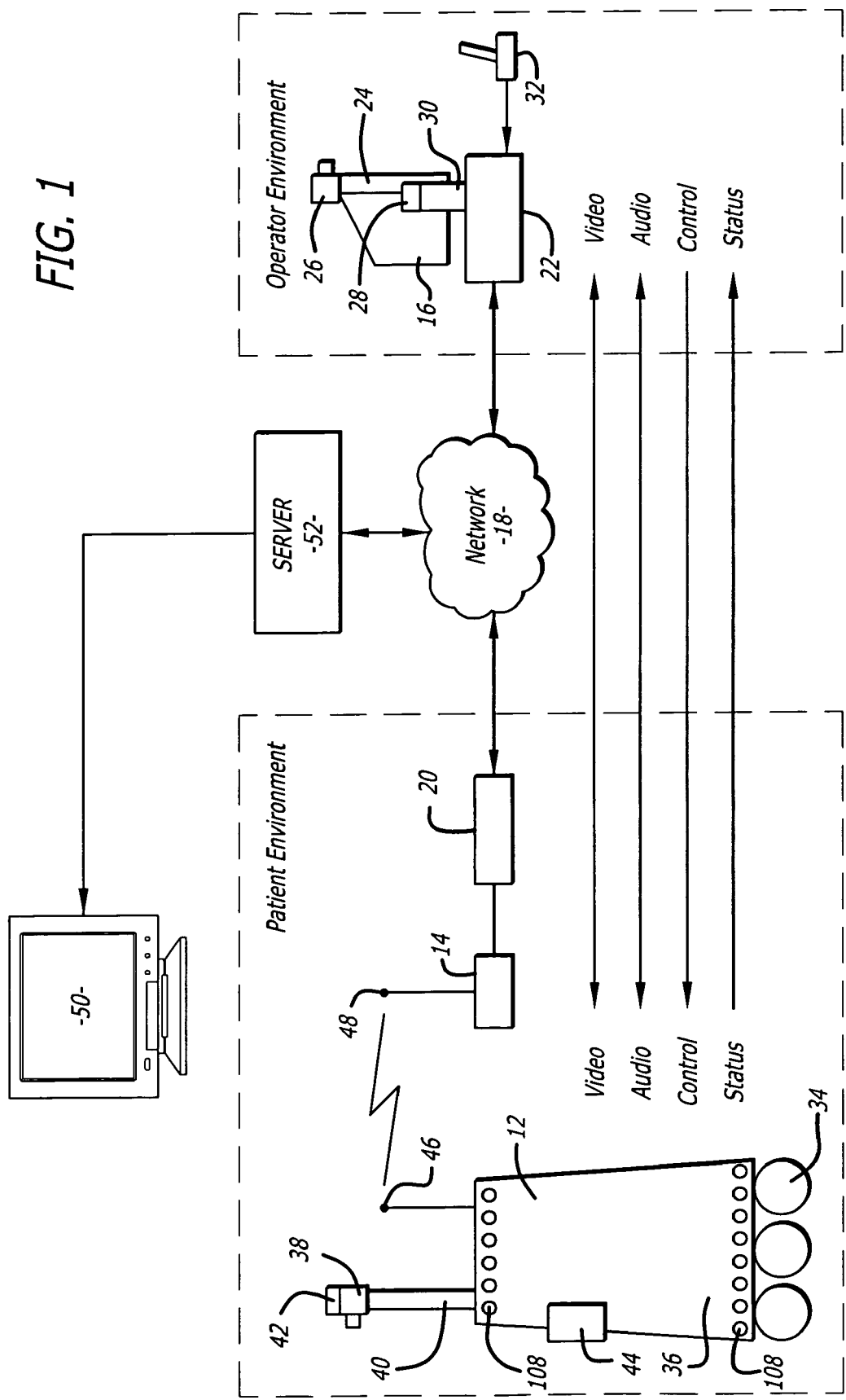
FIG. 1 is an illustration of a robotic system.

Referring to the drawings more particularly by reference numbers, FIG. 1 shows a system 10. The robotic system includes a robot 12, a base station 14 and a remote control station 16. The remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device. By way of example, the base station 14 may be a wireless router. Alternatively, the robot 12 may have a direct connection to the network thru for example a satellite.

The remote control station 16 may include a computer 22 that has a monitor 24, a camera 26, a microphone 28 and a speaker 30. The computer 22 may also contain an input device 32 such as a joystick or a mouse. The control station 16 is typically located in a place that is remote from the robot 12. Although only one remote control station 16 is shown, the system 10 may include a plurality of remote stations. In general any number of robots 12 may be controlled by any number of remote stations 16 or other robots 12. For example, one remote station 16 may be coupled to a plurality of robots 12, or one robot 12 may be coupled to a plurality of remote stations 16, or a plurality of robots 12.

Each robot 12 includes a movement platform 34 that is attached to a robot housing 36. Also attached to the robot housing 36 are a camera 38, a monitor 40, a microphone(s) 42 and a speaker(s) 44. The microphone 42 and speaker 30 may create a stereophonic sound. The robot 12 may also have an antenna 46 that is wirelessly coupled to an antenna 48 of the base station 14. The system 10 allows a user at the remote control station 16 to move the robot 12 through operation of the input device 32. The robot camera 38 is coupled to the remote monitor 24 so that a user at the remote station 16 can view a patient. Likewise, the robot monitor 40 is coupled to the remote camera 26 so that the patient may view the user. The microphones 28 and 42, and speakers 30 and 44, allow for audible communication between the patient and the user. The monitor 40 and camera 38 may move together in two degrees of freedom such as pan and tilt.

The remote station computer 22 may operate Microsoft OS software and WINDOWS XP or other operating systems such as LINUX. The remote computer 22 may also operate a video driver, a camera driver, an audio driver and a joystick driver.

The video images may be transmitted and received with compression software such as MPEG CODEC.

The system 10 includes a patient monitor 50 that can display patient information. The patient monitor 50 is typically located within a patient's room at a healthcare facility. The patient monitor 50 can be any type of device that can display graphics, video images and text. By way of example, the patient monitor 50 may be a CRT monitor, flat screen, or a laptop computer.

The remote station 16 and patient monitor 50 may be coupled to a server 52 through the network 18. The server 52 may contain electronic medical records of a patient. By way of example, the electronic medical records may include written records of treatment, patient history, medication information, a medical image, such as an x-ray, MRI or CT scan, EKGs, laboratory results, physician notes, etc. The medical records can be retrieved from the server 52 and displayed by the patient monitor 50. The remote station 16 may allow the physician to modify the records and then store the modified records back in the server 52. Although a server 52 is shown and described, it is to be understood that the information may be transferred directly from the remote station 16 to the patient monitor 50 without the server 52. Although a medical application is described, it is to be understood that the system may be used in a non-medical application. For example, the monitor can be a computer monitor at an office or home, and the information can be business or personal in nature.

Figure 2:
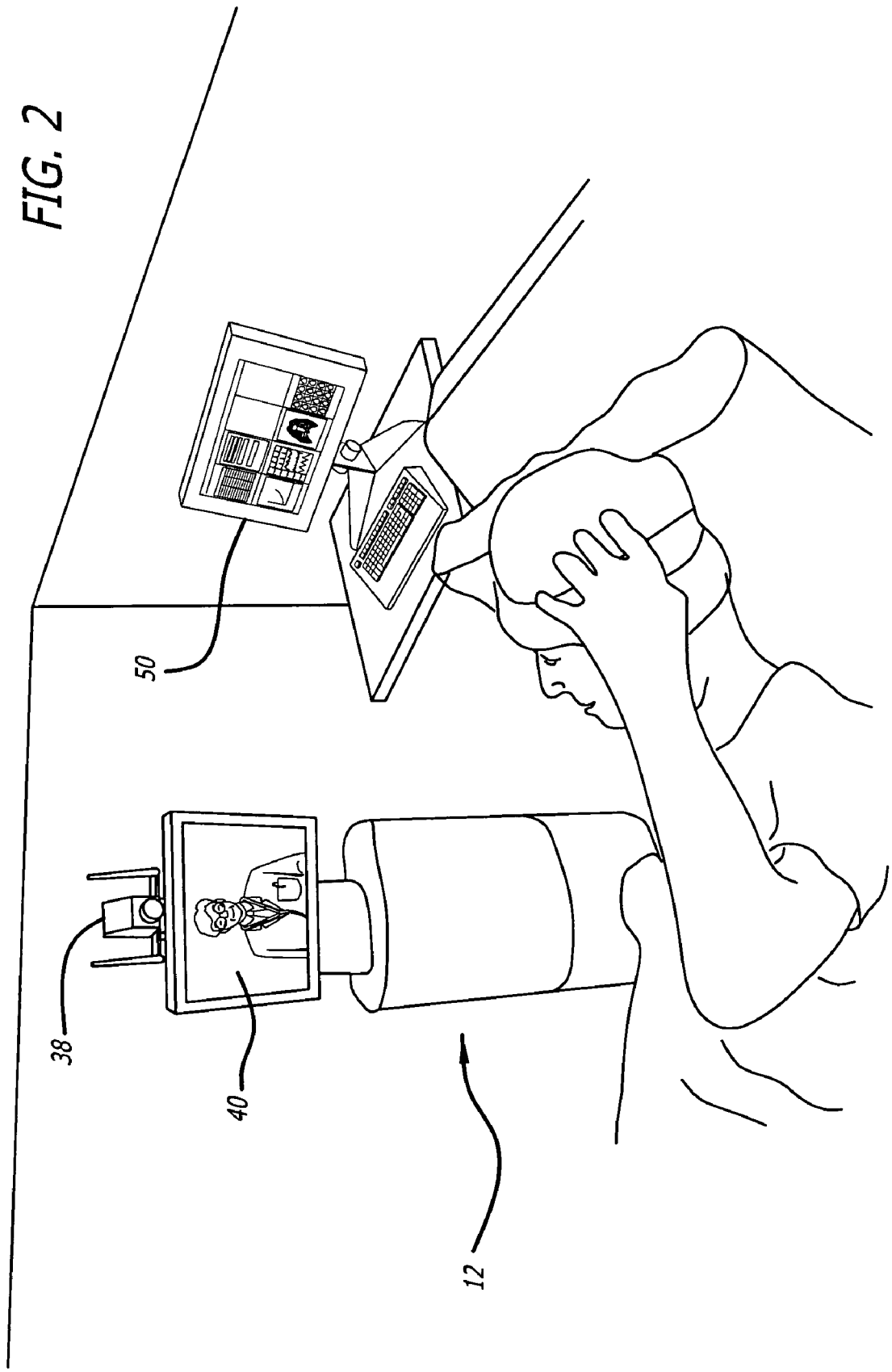
FIG. 2 is an illustration of the robotic system being used to provide physician consultation to a patient.

As shown in FIG. 2, the system allows a physician to review medical information with a patient. The robot 12 displays an image of the physician so that the physician's presence is projected into a patient's room. The patient monitor 50 displays medical information that can be reviewed by the patient. The robot camera 38 allows the physician to see the patient and to view the medical information displayed by the patient monitor 50. By way of example, the patient monitor 50 can display an x-ray of the patient and the physician can discuss the x-ray with the patient through the two-way video conferencing function of the system. The system may also allow the physician to highlight features of the x-ray with a tele-strating function.

Figure 3:
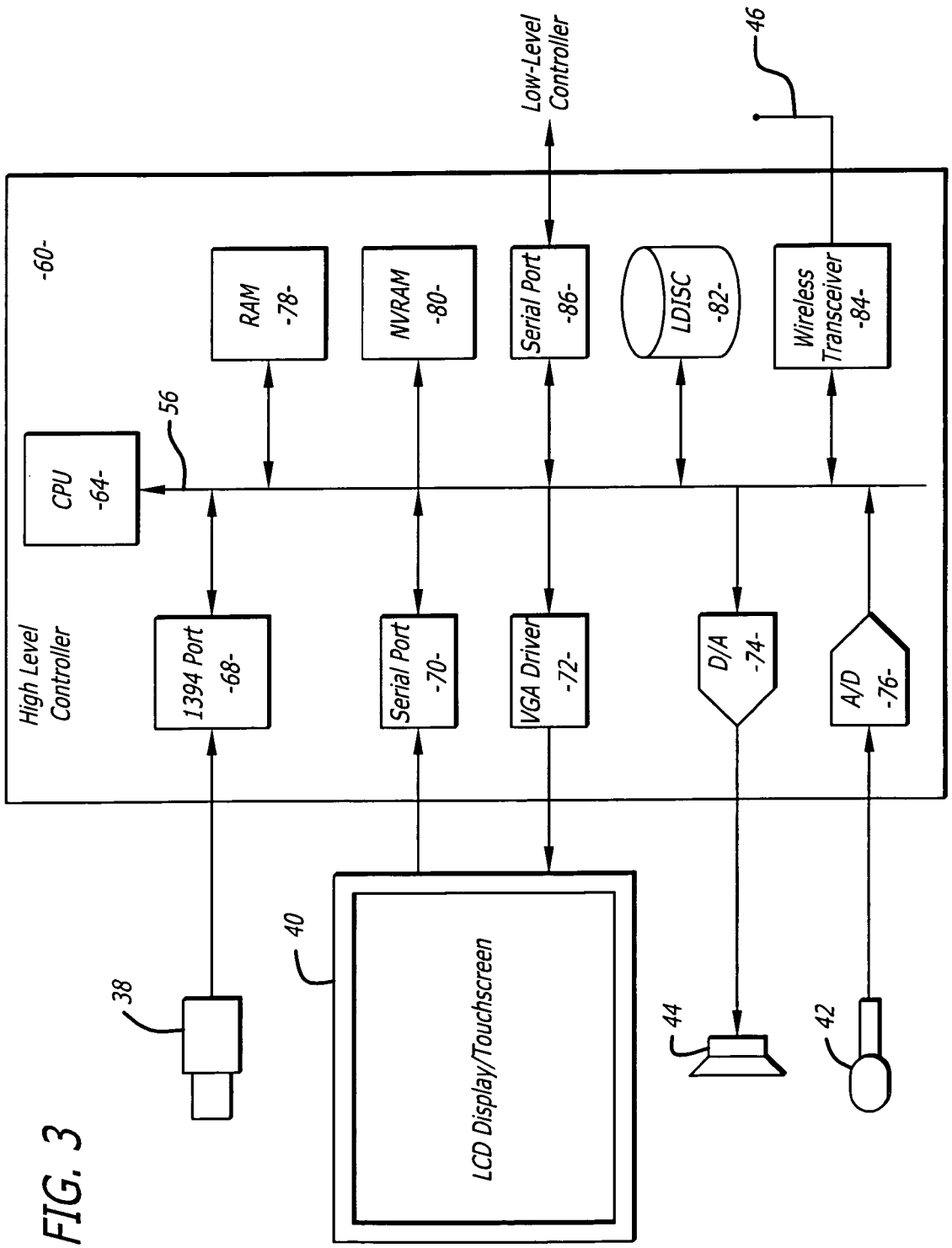
FIG. 3 is a schematic of an electrical system of a robot.
Figure 4:
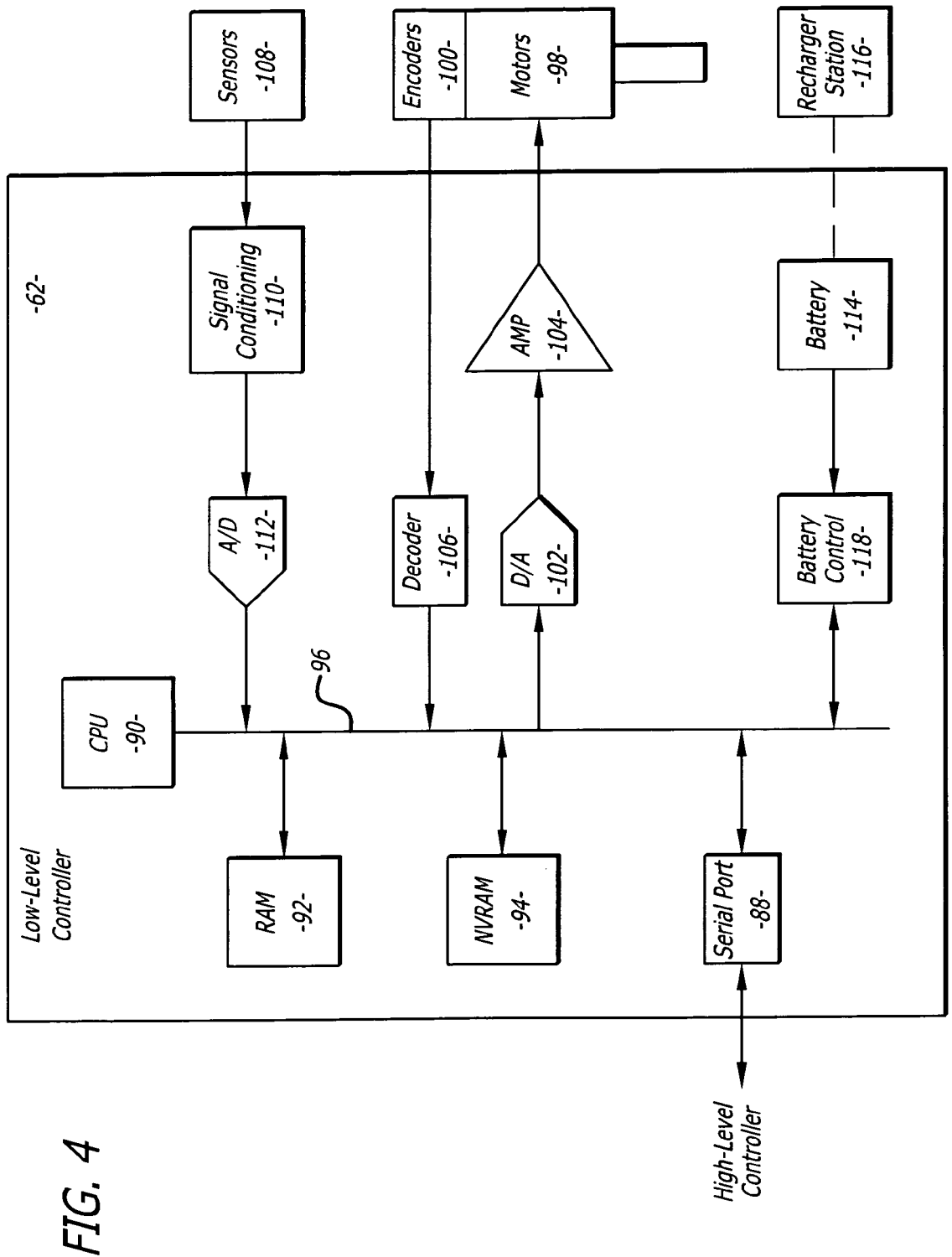
FIG. 4 is a further schematic of the electrical system of the robot.

FIGS. 3 and 4 show an embodiment of a robot 12. Each robot 12 may include a high level control system 60 and a low level control system 62. The high level control system 60 may include a processor 64 that is connected to a bus 66. The bus is coupled to the camera 38 by an input/output (I/O) port 68, and to the monitor 40 by a serial output port 70 and a VGA driver 72. The monitor 40 may include a touchscreen function that allows the patient to enter input by touching the monitor screen.

The speaker 44 is coupled to the bus 66 by a digital to analog converter 74. The microphone 42 is coupled to the bus 66 by an analog to digital converter 76. The high level controller 60 may also contain random access memory (RAM) device 78, a non-volatile RAM device 80 and a mass storage device 82 that are all coupled to the bus 72. The mass storage device 82 may contain medical files of the patient that can be accessed by the user at the remote control station 16. For example, the mass storage device 82 may contain a picture of the patient. The user, particularly a health care provider, can recall the old picture and make a side by side comparison on the monitor 24 with a present video image of the patient provided by the camera 38. The robot antennae 46 may be coupled to a wireless transceiver 84. By way of example, the transceiver 84 may transmit and receive information in accordance with IEEE 802.11b. The transceiver 84 may also process signals from the medical monitoring device in accordance with IEEE also known as Bluetooth. The robot may have a separate antennae to receive the wireless signals from the medical monitoring device.

The controller 64 may operate with a LINUX OS operating system. The controller 64 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 60 operates to control communication between the robot 12 and the remote control station 16.

The high level controller 60 may be linked to the low level controller 62 by serial ports 86 and 88. The low level controller 62 includes a processor 90 that is coupled to a RAM device 92 and non-volatile RAM device 94 by a bus 96. Each robot 12 contains a plurality of motors 98 and motor encoders 100. The motors 98 can activate the movement platform and move other parts of the robot such as the monitor and camera. The encoders 100 provide feedback information regarding the output of the motors 98. The motors 98 can be coupled to the bus 96 by a digital to analog converter 102 and a driver amplifier 104. The encoders 100 can be coupled to the bus 96 by a decoder 106. Each robot 12 also has a number of proximity sensors 108 (see also FIG. 1). The position sensors 108 can be coupled to the bus 96 by a signal conditioning circuit 110 and an analog to digital converter 112.

The low level controller 62 runs software routines that mechanically actuate the robot 12. For example, the low level controller 62 provides instructions to actuate the movement platform to move the robot 12. The low level controller 62 may receive movement instructions from the high level controller 60. The movement instructions may be received as movement commands from the remote control station or another robot. Although two controllers are shown, it is to be understood that each robot 12 may have one controller, or more than two controllers, controlling the high and low level functions.

The various electrical devices of each robot 12 may be powered by a battery(ies) 114. The battery 114 may be recharged by a battery recharger station 116. The low level controller 62 may include a battery control circuit 118 that senses the power level of the battery 114. The low level controller 62 can sense when the power falls below a threshold and then send a message to the high level controller 60.

The system may be the same or similar to a robotic system provided by the assignee InTouch-Health, Inc. of Santa Barbara, Calif. under the name RP-6 or RP-7, which is hereby incorporated by reference. The system may also be the same or similar to the system disclosed in application Ser. No. 10/206,457 published on Jan. 29, 2004, which is hereby incorporated by reference.

Figure 5:
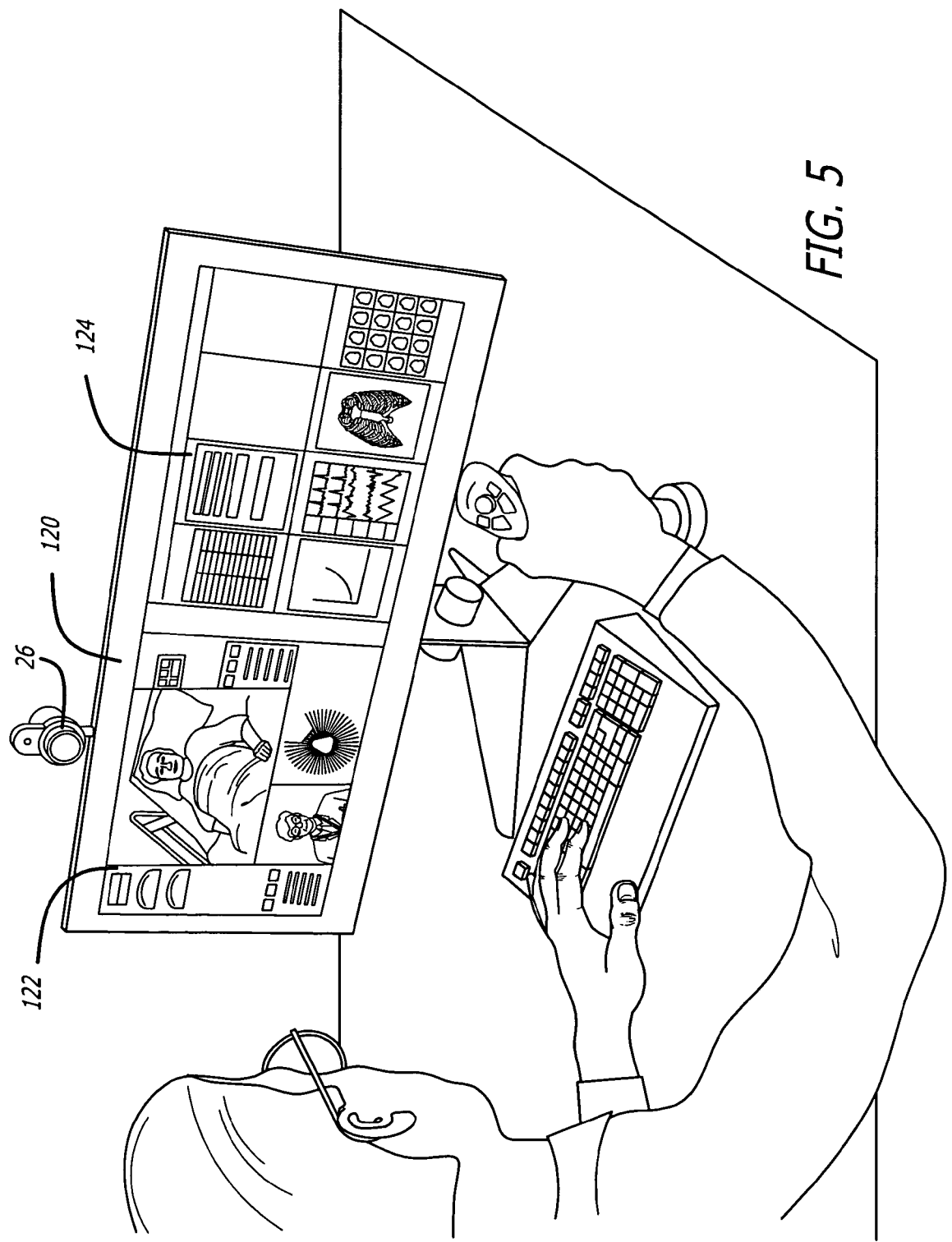
FIG. 5 is a display user interface of a remote station having a first screen field and a second screen field.

FIG. 5 shows a visual display 120 of the remote station. The visual display 120 displays a first screen field 122 and a second screen field 124. The two screen fields may be created by two different monitors. Alternatively, the two screen fields may be displayed by one monitor. The first and second screen fields 122 and 124 may be part of an application program(s) stored and operated by the computer 22 of the remote station 16.

Figure 6:
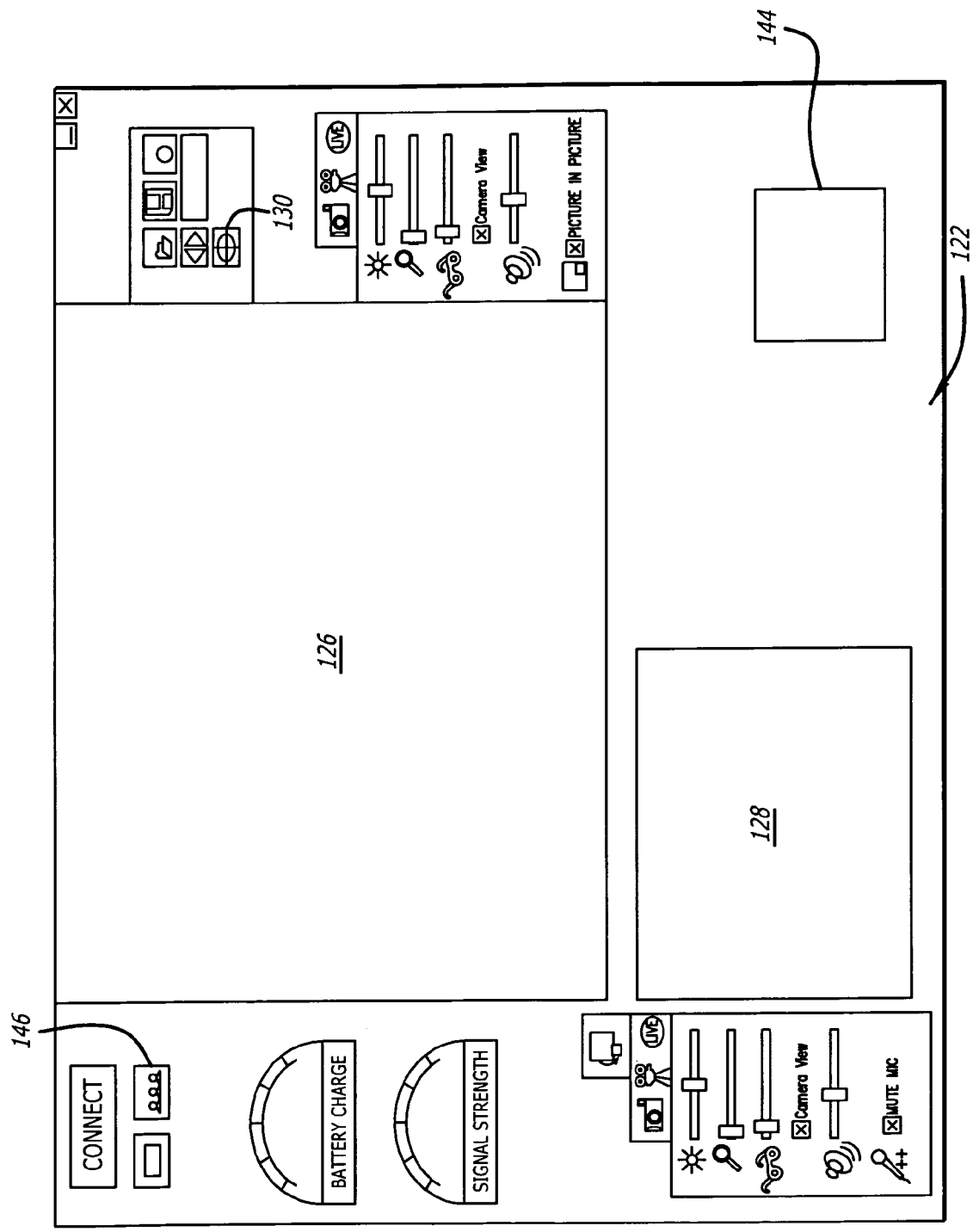
FIG. 6 is a display user interface showing a first screen field.

FIG. 6 shows a first screen field 122. The first screen field 122 may include a robot view field 126 that displays a video image captured by the camera of the robot. The first field 122 may also include a station view field 128 that displays a video image provided by the camera of the remote station. The first field 122 may have a capture button 130 that can be selected to move at least a portion of the record field 124 into the robot view field 126.

Figure 7:
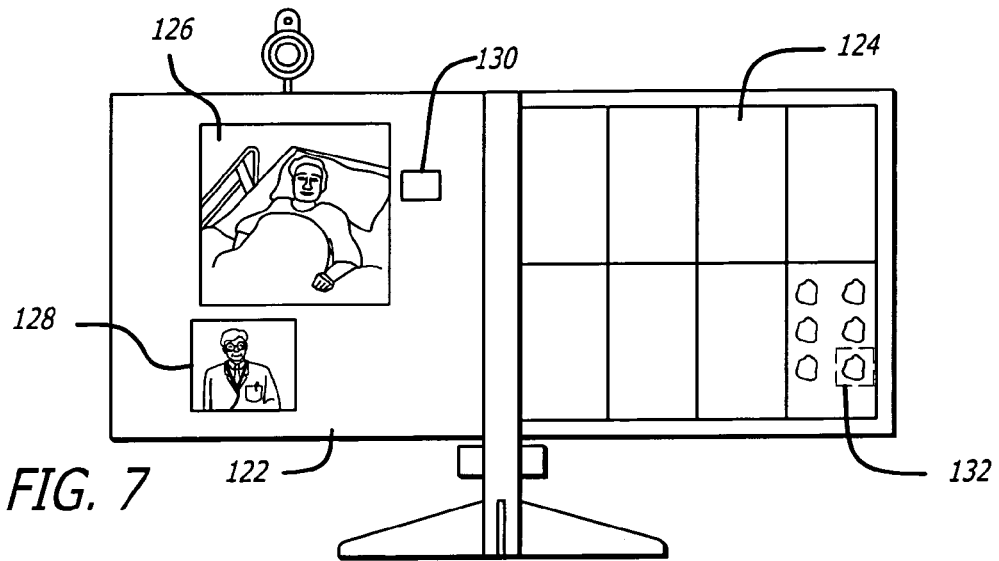
FIG. 7 is a display user interface showing a portion of the second screen field being highlighted.
Figure 8:
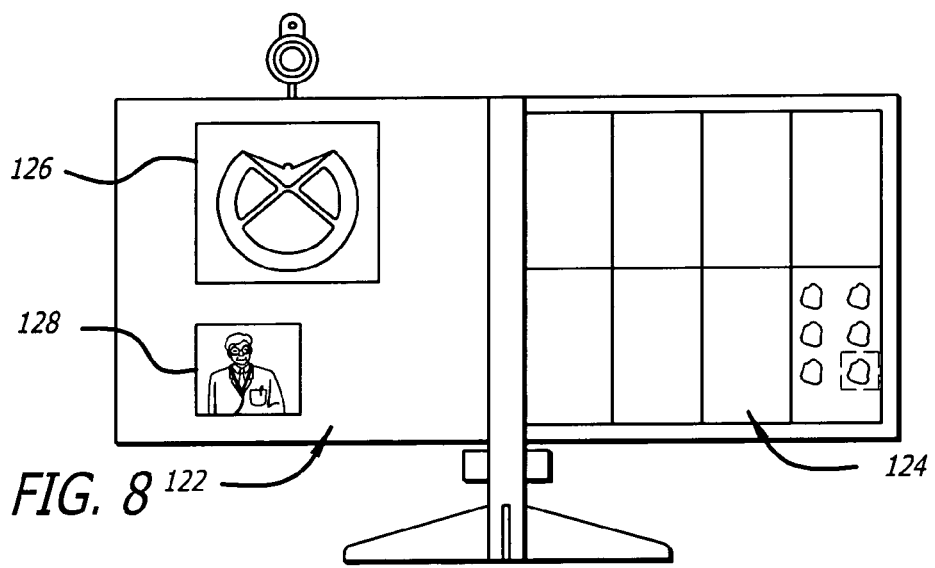
FIG. 8 is a display user interface showing the highlighted portion of the second screen transferred to the first screen.

As shown in FIGS. 7 and 8, the highlighted portion 132 of the second screen 124 may be copied to the robot view field 126. By way of example, a graphical rectangle may be drawn around a portion of the second field through manipulation of a mouse. The ability to create the rectangle may be enabled by the selection of the capture button 130. The highlighted portion of the second screen 132 may automatically populate the robot view field 126 when the rectangle is completed by the user.

Figure 9:
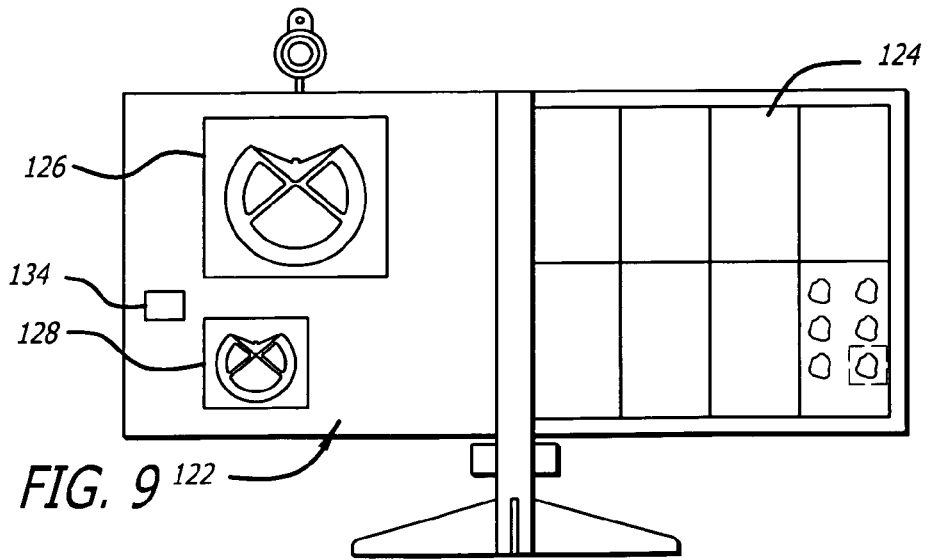
FIG. 9 is a display user interface showing the highlighted portion of the screen shared with the robot monitor.
Figure 10:
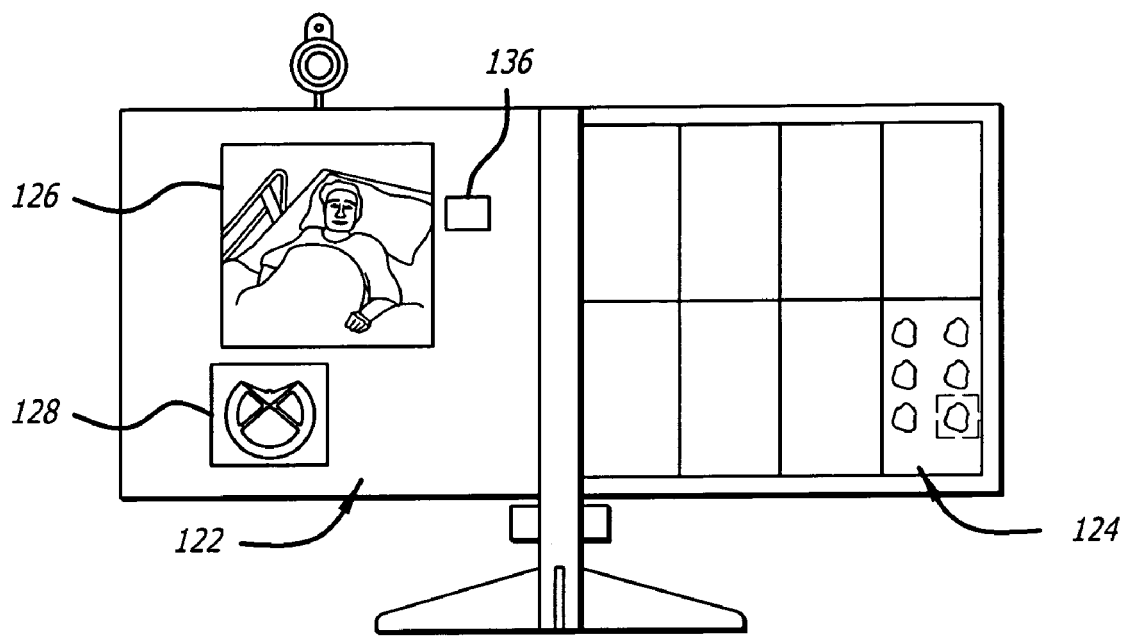
FIG. 10 is a display user interface showing a live robot camera feed.
Figure 11:
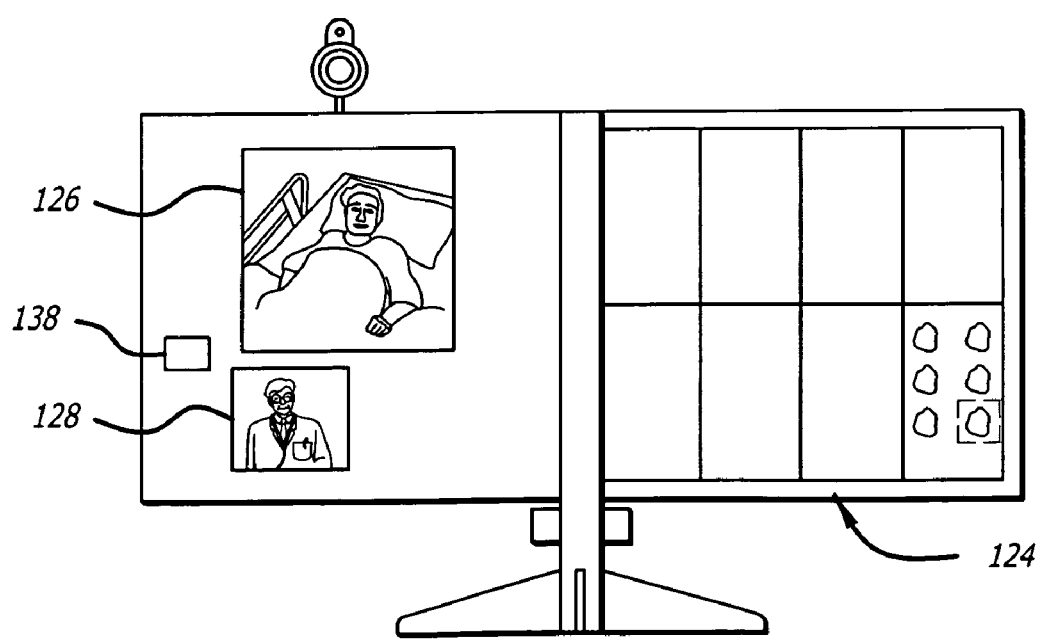
FIG. 11 is a display user interface showing a live remote station camera feed.

As shown in FIG. 9, the first screen field 122 may have a share button 134 that transfers the contents of the robot image field to the robot monitors. In this manner, the user can transfer the highlighted portion of the second screen field to the robot monitor. The transferred robot field contents are also displayed in the station view field 128. The user can switch back to a live feed from the robot camera by selecting the live button 136, as shown in FIG. 10. Likewise, the robot monitor may display a live feed of the remote station operator by selecting the live button 138, as shown in FIG. 11.

Referring to FIG. 6, the field 122 may have a button 144 that can be selected to transfer the contents of the second screen field 124 to the patient monitor 50. The system may provide the ability to annotate the image displayed in field 126 and/or 128. For example, a doctor at the remote station may annotate some portion of the image captured by the robot camera. The annotated image may be stored by the system. The system may also allow for annotation of images sent to the patient monitor 50 through the button 140. For example, a doctor may send a medical image, such as an x-ray, MRI or CT scan to the patient monitor. The medical image is displayed by the patient monitor 50. The doctor can annotate the medical image to point out a portion of the medical image to personnel located at the robot site. This allows the doctor to review the information with the patient as shown in FIG. 2.

The second screen field may display a variety of different applications. For example, the second field 124 may display patient records, a medical image, etc. By way of example, the record field 124 may be a medical records program provided by Global Care Quest Corp. of Los Angeles, Calif.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A medical system for a patient, comprising:
   a patient monitor that displays patient information;
   a mobile robot that has a robot monitor, and a robot camera that captures an image, said robot camera being capable of viewing the patient and said patient monitor; and
   a remote station that is coupled to said mobile robot, said remote station includes a remote station monitor that displays the image captured by said robot camera and a remote station camera that captures an image that is displayed by said robot monitor.

2. The system of claim 1, further comprising a server that is coupled to said remote station and said patient monitor and provides said patient information.

3. The system of claim 1, wherein said patient information is displayed by said remote station monitor.

4. The system of claim 1, further comprising a broadband network that is coupled to said remote station and said mobile robot.

5. The system of claim 1, wherein said robot monitor and said robot camera move together in at least one degree of freedom.

6. The system of claim 1, wherein said patient information includes a medical image.

7. A method for interacting with a patient, comprising:
   moving a mobile robot that has a camera to view a patient and a patient monitor;
   displaying patient information on the patient monitor; and,
   conducting a two-way video conference between the patient, and a medical personnel at a remote station that controls movement of the robot.

8. The method of claim 7, wherein the patient information is provided by the remote station.

9. The method of claim 7, wherein the patient information is provided by a server.

10. The method of claim 7, wherein the patient information is displayed by a remote station monitor.

11. The method of claim 7, further comprising transmitting robot control commands from the remote station to the mobile robot through a broadband network.

12. The method of claim 7, further comprising moving together a robot camera and a robot monitor in at least one degree of freedom.

13. The method of claim 7, wherein the patient information includes a medical image.

* * * * *